United States Patent
Schneiderman

Patent Number: 6,142,926
Date of Patent: Nov. 7, 2000

[54] RADIATION DOSE DELIVERY CATHETER WITH REINFORCING MANDREL

[75] Inventor: Gary Schneiderman, San Ramon, Calif.

[73] Assignee: Advanced Cardiovascular Systems, Inc., Santa Clara, Calif.

[*] Notice: This patent is subject to a terminal disclaimer.

[21] Appl. No.: 09/118,134

[22] Filed: Jul. 16, 1998

Related U.S. Application Data

[63] Continuation of application No. 08/705,945, Aug. 29, 1996, Pat. No. 5,782,740.

[51] Int. Cl.$^7$ ............................................. A61N 5/00
[52] U.S. Cl. ............................................................ 600/3
[58] Field of Search ........................... 600/1–8; 604/264, 604/280, 282

[56] References Cited

U.S. PATENT DOCUMENTS

| | | |
|---|---|---|
| 4,581,017 | 4/1986 | Sahota . |
| 4,661,094 | 4/1987 | Simpson . |
| 4,697,575 | 10/1987 | Horowitz . |
| 4,706,652 | 11/1987 | Horowitz . |

(List continued on next page.)

FOREIGN PATENT DOCUMENTS

| | | |
|---|---|---|
| 0 633 041 A1 | 1/1995 | European Pat. Off. . |
| 0 688 580 A1 | 12/1995 | European Pat. Off. . |
| 0801961 | 4/1997 | European Pat. Off. . |
| 082271 | 9/1997 | European Pat. Off. . |
| 0865803 | 3/1998 | European Pat. Off. . |
| 0879614 | 5/1998 | European Pat. Off. . |
| 4 315 002 | 5/1993 | Germany . |
| 9102312 | 2/1991 | Greece . |
| WO 92/17236 | 10/1992 | WIPO . |
| WO 93/04735 | 3/1993 | WIPO . |
| WO 94/25106 | 11/1994 | WIPO . |
| WO 95/19807 | 7/1995 | WIPO . |
| WO 95/26681 | 10/1995 | WIPO . |
| WO 96/10436 | 4/1996 | WIPO . |
| WO97/40889 | 4/1997 | WIPO . |
| WO98/01182 | 5/1997 | WIPO . |
| WO98/01183 | 7/1997 | WIPO . |
| WO98/01184 | 7/1997 | WIPO . |
| WO98/01185 | 7/1997 | WIPO . |
| WO98/39052 | 1/1998 | WIPO . |

OTHER PUBLICATIONS

Lindsay, et al., Aortic Arteriosclerosis in the Dog After Localized Aortic X–Irradiation, *Circulation Research*, vol. X, Jan. 1962.

Friedman, et al., The Antiatherogenic Effect of Iridium$^{192}$ Upon the Coloesterol–Fed Rabbit, *Journal of Clinical Investigation*, 1964.

(List continued on next page.)

*Primary Examiner*—Samuel G. Gilbert
*Attorney, Agent, or Firm*—Blakely Sokoloff Taylor & Zafman, LLP

[57] ABSTRACT

The invention is directed to a rapid exchange type intravascular catheter suitable for maintaining patency of a body lumen for a period of time sufficient to permit delivery of a radiation source to the body lumen. The catheter utilizes a reinforcing mandrel to improve the pushability and strength of the catheter as it tracks along a guide wire, and permits blood flow through an inflatable member while radiation therapy is being provided.

7 Claims, 3 Drawing Sheets

U.S. PATENT DOCUMENTS

| | | |
|---|---|---|
| 4,744,366 | 5/1988 | Jang . |
| 4,748,982 | 6/1988 | Horzewski et al. . |
| 4,762,130 | 8/1988 | Fogarty et al. . |
| 4,763,671 | 8/1988 | Goffinet . |
| 4,771,777 | 9/1988 | Horzewski et al. . |
| 4,771,778 | 9/1988 | Mar . |
| 4,775,371 | 10/1988 | Mueller, Jr. . |
| 4,790,315 | 12/1988 | Mueller, Jr. et al. . |
| 4,815,449 | 3/1989 | Horowitz . |
| 4,861,520 | 8/1989 | van't Hooft et al. . |
| 4,936,823 | 6/1990 | Colvin et al. . |
| 4,940,064 | 7/1990 | Desai . |
| 4,969,863 | 11/1990 | van't Hooft et al. . |
| 4,976,720 | 12/1990 | Machold et al. . |
| 4,983,167 | 1/1991 | Sahota . |
| 4,994,560 | 2/1991 | Kruper, Jr. et al. . |
| 4,998,917 | 3/1991 | Gaiser et al. . |
| 5,002,560 | 3/1991 | Machold et al. . |
| 5,015,230 | 5/1991 | Martin et al. . |
| 5,016,042 | 5/1991 | Sahota . |
| 5,032,113 | 7/1991 | Burns . |
| 5,034,001 | 7/1991 | Garrison et al. . |
| 5,046,503 | 9/1991 | Schneiderman . |
| 5,059,166 | 10/1991 | Fischell et al. . |
| 5,061,273 | 10/1991 | Yock . |
| 5,084,002 | 1/1992 | Liprie . |
| 5,100,429 | 3/1992 | Sinofsky et al. . |
| 5,133,956 | 7/1992 | Garlich et al. . |
| 5,137,513 | 8/1992 | McInnes et al. . |
| 5,176,661 | 1/1993 | Evard et al. . |
| 5,180,368 | 1/1993 | Garrison . |
| 5,195,971 | 3/1993 | Sirhan . |
| 5,199,939 | 4/1993 | Dake et al. . |
| 5,213,561 | 5/1993 | Weinstein et al. . |
| 5,226,889 | 7/1993 | Sheiban . |
| 5,242,396 | 9/1993 | Evard . |
| 5,258,419 | 11/1993 | Rolando et al. . |
| 5,263,963 | 11/1993 | Garrison . |
| 5,267,960 | 12/1993 | Hayman et al. . |
| 5,273,738 | 12/1993 | Matthews et al. . |
| 5,279,562 | 1/1994 | Sirhan et al. . |
| 5,282,781 | 2/1994 | Liprie . |
| 5,295,959 | 3/1994 | Gurbel et al. . |
| 5,295,960 | 3/1994 | Aliahmad et al. . |
| 5,295,995 | 3/1994 | Kleiman . |
| 5,300,281 | 4/1994 | McMillan et al. . |
| 5,302,168 | 4/1994 | Hess . |
| 5,306,246 | 4/1994 | Sahatjian et al. . |
| 5,308,356 | 5/1994 | Blackshear, Jr. et al. . |
| 5,320,824 | 6/1994 | Brodack et al. . |
| 5,334,154 | 8/1994 | Samson et al. . |
| 5,336,518 | 8/1994 | Narayanan et al. . |
| 5,350,361 | 9/1994 | Tsukashima et al. . |
| 5,352,199 | 10/1994 | Tower . |
| 5,354,257 | 10/1994 | Roubin et al. . |
| 5,380,747 | 1/1995 | Medford et al. . |
| 5,395,333 | 4/1995 | Brill . |
| 5,405,622 | 4/1995 | Vernice et al. . |
| 5,409,495 | 4/1995 | Osborn . |
| 5,411,466 | 5/1995 | Hess . |
| 5,415,664 | 5/1995 | Pinchuk . |
| 5,441,516 | 8/1995 | Wang et al. . |
| 5,447,497 | 9/1995 | Sogard et al. . |
| 5,456,667 | 10/1995 | Ham et al. . |
| 5,458,572 | 10/1995 | Campbell et al. . |
| 5,484,384 | 1/1996 | Fearnot . |
| 5,498,227 | 3/1996 | Mawad . |
| 5,503,613 | 4/1996 | Weinberger . |
| 5,503,614 | 4/1996 | Liprie . |
| 5,507,301 | 4/1996 | Wasicek et al. . |
| 5,507,769 | 4/1996 | Marin et al. . |
| 5,516,336 | 5/1996 | McInnes et al. . |
| 5,540,659 | 7/1996 | Teirstein . |
| 5,542,925 | 8/1996 | Orth . |
| 5,573,508 | 11/1996 | Thornton . |
| 5,573,509 | 11/1996 | Thornton . |
| 5,616,114 | 4/1997 | Thornton et al. . |
| 5,618,266 | 4/1997 | Liprie . |
| 5,643,171 | 7/1997 | Bradshaw et al. . |
| 5,653,691 | 8/1997 | Rupp et al. . |
| 5,683,345 | 11/1997 | Waksman et al. . |
| 5,688,486 | 11/1997 | Watson et al. . |
| 5,707,332 | 1/1998 | Weinberger . |
| 5,730,698 | 3/1998 | Fischell et al. . |
| 5,782,740 | 7/1998 | Schneiderman ............................ 600/1 |
| 5,840,067 | 11/1998 | Berguer et al. . |
| 5,851,171 | 12/1998 | Gasson . |
| 5,871,436 | 2/1999 | Eury . |
| 5,910,101 | 6/1999 | Andrews et al. . |
| 5,938,582 | 8/1999 | Ciamacco, Jr. et al. . |

OTHER PUBLICATIONS

Friedman, et al., Effect of Iridium$^{192}$ Radiation on Thromboatherosclerotic Plaque in the Rabbit Aorta, *Arch Path,* vol. 80, Sep. 1965.

Hoopes, et al., Intraoperative Irradiation of the Canine Abdominal Aorta and Vena Cava, *Int'l Journal Radiation Oncology, Biology, Physics,* vol. 13, No. 5, May 1987.

Weshler, et al., Inhibition by Irradiation of Smooth Muscle Cell Proliferation in the De–Endothelialized Rat Aorta, 21st Meeting—European Society for Radiation Biology, collected in *Frontiers of Radiation Biology,* 1988.

Dawson, John T., Theoretic Considerations Regarding Low––Dose Radiation Therapy for Prevention of Restenosis After Angioplasty, *Texas Heart Institute Journal,* vol. 18, No. 1, 1991.

Johnson, M.D., et al., Review of Radiation Safety in the Cardiac Catheterization Laboratory, *Catheterization and Cardiovascular Diagnosis,* 1992.

Schwartz, M.D., et al., Effect of External Beam Irradiation on Neointimal Hyperplasia After Experimental Coronary Artery Injury, *Journal of the American College of Cardiology,* vol. 19, No. 5, Apr. 1992.

March, M.D., et al., *8–Methoxypsoralen and Longwave Ultraviolet Irradiation Are a Novel Antiproliferative Combination for Vascular Smooth Muscle,* Krannert Institute of Cardiology, Sep. 1992.

Katzen, Barry T., M.D., *Mechanical Approaches to Restenosis in the Peripheral Circulation,* Miami Vascular Institute at Baptist Hospital (Undated).

Hunink, M.D., et al., Risks and Benefits of Femoropopliteal Percutaneous Balloon Angioplasty, *Journal of Vascular Surgery,* vol. 17, No. 1, Jan. 1993.

Weintraub, M.D., et al., Can Restenosis After Coronary Angioplasty be Predicted From Clinical Variables?, *Journal of the American College of Cardiology,* vol. 21, No. 1, Jan. 1993.

Kuntz, M.D., et al., Generalized Model of Restenosis After Conventional Balloon Angioplasty, Stenting and Directional Atherectomy, *Journal of the American College of Cardiology,* vol. 21, No. 1, Jan. 1993.

Haude, M.D., Quantitative Analysis of Elastic Recoil After Balloon Angioplasty and After Intracoronary Implantation of Balloon–Expandable Palmaz–Schatz Stents, *Journal of the American College of Cardiology,* vol. 21, No. 1, Jan. 1993.

Schwartz, et al., Differential Neointimal Response to Coronary Artery Injury in Pigs and Dogs, Implications for Restenosis Models, *Arteriosclerosis and Thrombosis*, vol. 14, No. 3, Mar. 1994.

Liermann, et al., Prophylactic Endovascular Radiotherapy to Prevent Intimal Hyperplasia After Stent Implantation in Femoropopliteal Arteries, *CardioVascular and Interventional Radiology* (1994).

Wiedermann, et al., Effects of High–Dose Intracoronary Irradiation on Vasomotor Function and Smooth Muscle Histopathology, *Intracoronary Irradiation and Vasomotion*, Jan. 1994.

Wagner, et al., Potential Biological Effects Following High X–Ray Dose Interventional Procedures, *Journal of Vascular and Interventional Radiology*, Jan.–Feb. 1994, pp. 71–84.

Wiedermann, M.D., et al., Intracoronary Irradiation Markedly Reduces Restenosis After Balloon Angioplasty in a Porcine Model, *Journal of the American College of Cardiology*, vol. 23, No. 6, May 1994.

Kakuta, M.D., et al., Differences in Compensatory Vessel Enlargement, No Intimal Formation, Account for Restenosis After Angioplasty in the Hypercholesterolemic Rabbit Model, *Circulation Research*, vol. 89, No. 6, Jun. 1994.

Fischell, M.D., et al., Low–Dose, β–Particle Emission from 'Stent' Wire Results in Complete, Localized Inhibition of Smooth Muscle Cell Proliferation, *Circulation Research*, vol. 90, No. 6, Dec. 1994.

Waksman, M.D., et al., Endovascular Low–Dose Irradiation Inhibits Neointima Formation After Coronary Artery Balloon Injury in Swine: A Possible Role for Radiation Therapy in Restenosis Prevention, *Circulation Research*, vol. 91, No. 5, Mar. 1, 1995.

Wiedermann, M.D., Intracoronary Irradiation Markedly Reduces Neointimal Proliferation After Balloon Angioplasty in Swine: Persistent Benefit at 6–Month Follow–Up, *Journal of the American College of Cardiology*, vol. 25, No. 6, May 1995.

Waksmann, M.D., et al., Intracoronary Radiation Before Stent Implantation Inhibits Neointima Formation in Stented Porcine Coronary Arteries, *Circulation Research*, vol. 92, No. 6, Sep. 15, 1995.

Verin, M.D., et al., Intra–Arterial Beta Irradiation Prevents Neointimal Hyperplasia in a Hypercholesterolemic Rabbit Restenosis Model, *Circulation Research*, vol. 92, No. 8, Oct. 15, 1995.

Waksman, M.D., et al., Intracoronary Low–Dose β–Irradiation Inhibits Neointima Formation After Coronary Artery Balloon Injury in the Swine Restenosis Model, *Circulation Research*, vol. 92, No. 10, Nov. 15, 1995.

Hehrlein, C., et al., Radioactive Stents, *Discoveries in Radiation for Restenosis*, Abstract 22 (Jan. 1996).

Fischell, Tim A., M.D., A Beta–Particle Emitting Radioisotope Stent for the Prevention of Restenosis, *Discoveries in Radiation for Restenosis*, Abstract 23 (Jan. 1996).

Li, et al., A Novel Brachyehtapy Source for Treatment of Coronary Artery Restenosis, *Discoveries in Radiation for Restenosis*, Abstract 24 (Jan. 1996).

Waksman, M.D., et al., Catheter–Based Radiation in Stented Arteries, *Discoveries in Radiation for Restenosis*, Abstract 25 (Jan. 1996).

Martin, Louis G., M.D., Radiation for Peripheral Applications: Technical Aspects, *Discoveries in Radiation for Restenosis*, Abstract 27 (Jan. 1996).

Lumsden, M.D., et al., Restenosis in Peripheral Vascular Disease, *Discoveries in Radiation for Restenosis*, Abstract 28 (Jan. 1996).

Schopohl, et al., Endovascular Irradiation for Avoidance or Recurrent Stenosis After Stent Implantation in Peripheral Arteries—5 Years Follow–Up, *Discoveries in Radiation for Restenosis*, Abstract 29 (Jan. 1996).

Waksman, M.D., et al., Radiation in the Peripheral System at Emory, *Discoveries in Radiation for Restenosis*, Abstract 30 (Jan. 1996).

Teirstein, et al., Catheter–Based Radiation Therapy to Inhibit Restenosis Following Coronary Stenting, *Discoveries in Radiation for Restenosis*, Abstract 31 (Jan. 1996).

King III, M.D., et al., Clinical Restenosis Trials Using Beta Energy Radiation, *Discoveries in Radiation for Restenosis*, Abstract 32 (Jan. 1996).

Urban, M.D., et al., Endovascular Irradiation With 90Y Wire, *Discoveries in Radiation for Restenosis*, Abstract 33 (Jan. 1996).

Condado, et al., Late Follow–Up After Percutaneous Transluminal Coronary Angioplasty (PTCA) and Intracoronary Radiation Therapy (ICRT), *Discoveries in Radiation for Restenosis*, Abstract 34 (Jan. 1996).

Weldon, Thomas D., Catheter Based Beta Radiation System, *Discoveries in Radiation for Restenosis*, Abstract 35 (Jan. 1996).

van't Hooft, et al., HDR Afterloader for Vascular Use, *Discoveries in Radiation for Restenosis*, Abstract 36 (Jan. 1996).

Fischell, Robert E., et al., The Radioisotope Stent: Conception and Implementation, *Discoveries in Radiation for Restenosis*, Abstract 37 (Jan. 1996).

Popowski, M.D., et al., Radioactive Wire in a Self–Centering Catheter System, *Discoveries in Radiation for Restenosis*, Abstract 38 (Jan. 1996).

Calfee, Richard V., Ph.D., High Dose Rate Afterloader System for Endovascular Use—Neocardia, *Discoveries in Radiation for Restenosis*, Abstract 39 (Jan. 1996).

Smith, Dr. Edward F., III, Issues on Handling Radioactive Devices to Prevent Restenosis, *Discoveries in Radiation for Restenosis*, Abstract 40 (Jan. 1996).

Unterberg, et al., Reduced Acute Thrombus Formation Results in Decreased Neointimal Proliferation After Coronary Angioplasty, collected in *Discoveries in Radiation for Restenosis—Selected Literature* (Jan. 1996).

Schwartz, et al., Effect of External Beam Irradiation on Neointimal Hyperplasia After Experimental Coronary Artery Injury, collected in *Discoveries in Radiation for Restenosis—Selected Literature* (Jan. 1996).

Hehrlein, et al., Low–Dose RadioactiveEndovascular Stents Prevent Smooth Muscle Cell Proliferation and Neointimal Hyperplasia in Rabbits, collected in *Discoveries in Radiation for Restenosis—Selected Literature* (Jan. 1996).

Soares, et al., Measurement of Radial Dose Distributions Around Small Beta Particle Emitters Using High Resolution Radiochromic Foil Dosimetry, *Nuclear Technology Publishing*, vol. 47, pp. 367–372 (Undated).

Byhardt, et al., The Heart and Blood Vessels, *Radiation Oncology: Rationale, Technique, Results*, Chapter Thirteen, pp. 277–284 (Undated).

PCT Search Report PCT/US 99/03343 mailed Jun. 17, 1999.

PCT Search Report PCT/US 99/03360 mailed Jun. 17, 1999.

PCT Search Report PCT/US 99/03327 mailed Jun. 18, 1999.

PCT Search Report PCT/US 99/03328 mailed Jun. 18, 1999.

PCT Search Report PCT/US 99/03329 mailed Jun. 18, 1999.

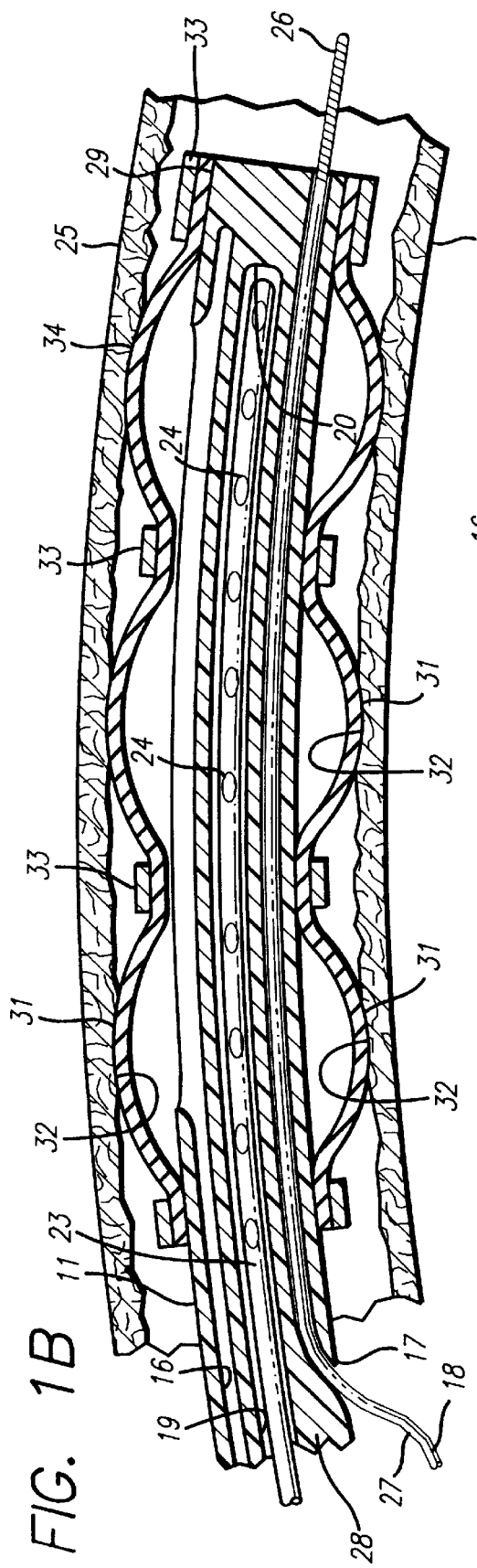
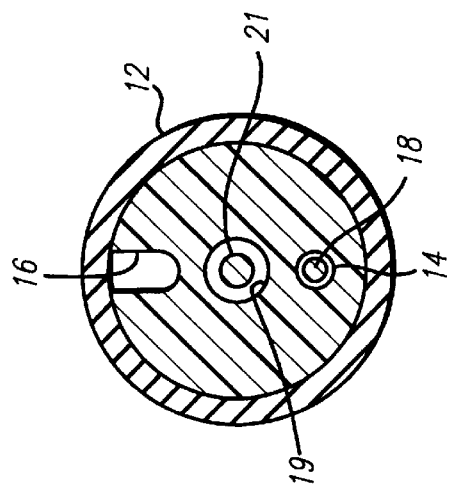
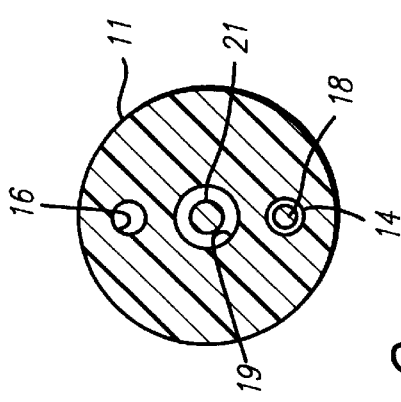
FIG. 1B
FIG. 3
FIG. 2

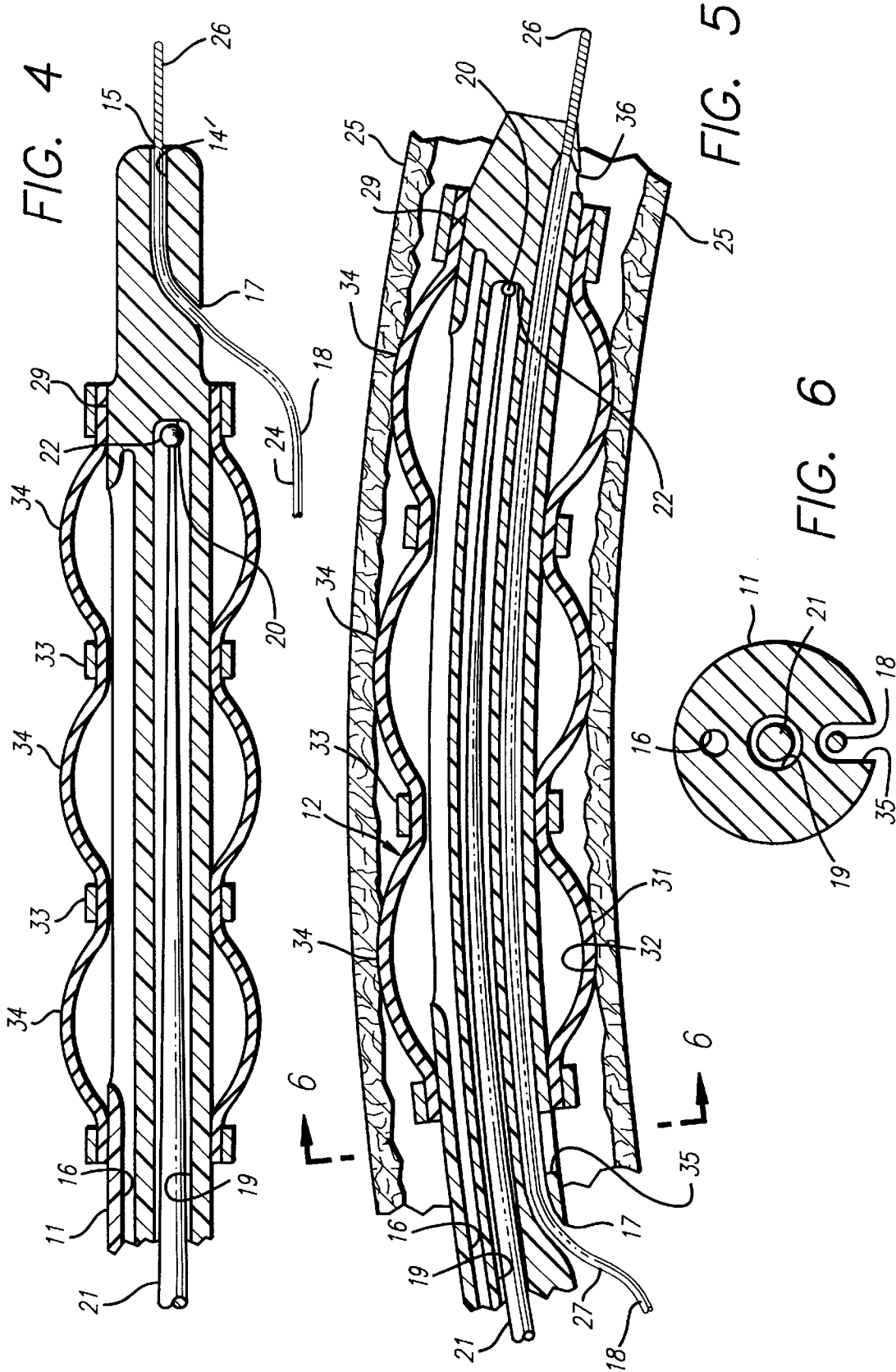

RADIATION DOSE DELIVERY CATHETER WITH REINFORCING MANDREL

This application is filed under 37 CFR 1.53(b) as a continuation of U.S. Ser. No. 08/705,945 filed Aug. 29, 1996 now U.S. Pat. No. 5,782,740.

BACKGROUND OF THE INVENTION

This invention generally relates to intravascular catheters for treating a portion of a body lumen with radiation and particularly to a rapid exchange type intravascular catheter suitable for delivering a radiation source to the body lumen which utilizes a reinforcing mandrel to improve the pushability, strength and trackability of the catheter as it moves along a guide wire.

In percutaneous transluminal coronary angioplasty (PTCA) procedures, a guiding catheter having a preshaped distal tip is percutaneously introduced into the cardiovascular system of a patient through the brachial or femoral artery and is advanced therein until the preshaped distal tip is disposed within the aorta adjacent to the ostium of the desired coronary artery. The guiding catheter is then twisted and torqued from its proximal end to turn its distal tip so that it can be guided into the coronary ostium. In an over-the-wire dilatation catheter system, a guide wire and a dilatation catheter having an inflatable balloon on the distal end thereof are introduced into, and advanced through, the proximal end of the guiding catheter to the distal tip of the guiding catheter seated within the coronary ostium. The distal tip of the guide wire is usually manually shaped (i.e. curved) by the physician or one of the attendants before it and the dilatation catheter are introduced into the guiding catheter. The guide wire is usually first advanced out of the distal end of the guiding catheter and is maneuvered into the patient's coronary vasculature containing the stenosis to be dilated, and is then advanced beyond the stenosis. Thereafter, the dilatation catheter is advanced over the guide wire until the dilatation balloon is positioned across the stenosis. Once the dilatation catheter is in position, the balloon of the catheter is filled with radiopaque liquid at relatively high pressures (e.g., generally about 4–18 atmospheres) to inflate it to a predetermined size (preferably the same as the normal inner diameter of the artery at that particular location) in order to radially expand the lumen at the stenosis, thereby increasing the effective diameter of the occluded artery. The balloon can then be deflated so that the catheter can be removed and blood flow resumed through the dilated artery.

A rapid exchange type catheter has a relatively short guide wire-receiving sleeve or inner lumen (sometimes referred to as "rail") extending a short distance through the distal portion of the catheter body. This inner lumen preferably extends approximately 10 cm, and typically about 30 to 40 cm, from a first guide wire port at the distal end of the catheter to a second side guide wire port located on the catheter body. In some catheters, the "rail" can be much smaller than 10 cm, especially when the side guide wire port is located distal to the inflation balloon. The catheter can be advanced within the patient's vascular system in much the same fashion as described above as the short, inner sleeve of the catheter slides along the length of the guide wire. Alternatively, the guide wire may be first advanced within the patient's vasculature until the distal end of the guide wire extends distally to the stenosis with the catheter then being mounted onto the proximal end of the in-place guide wire and advanced over the guide wire until the balloon portion is positioned across the stenosis. This particular structure allows for the rapid exchange of the catheter usually without the need for an exchange wire or adding a guide wire extension to the proximal end of the guide wire. Other over-the-wire or rapid exchange catheters can also be designed to utilize therapeutic or diagnostic means in place of the balloon in the description above.

One common problem that sometimes occurs after an angioplasty procedure has been performed is the development of restenosis at, or near, the original site of the stenosis. When restenosis occurs, a second angioplasty procedure or even bypass surgery may be required, depending upon the degree of restenosis. In order to prevent the need to perform bypass surgery or subsequent angioplasty procedures, various devices and procedures have been developed for reducing the likelihood of development of restenosis after arterial intervention. For example, an expandable tube (commonly termed "stent") designed for long term implantation with the body lumen has been utilized to help prevent restenosis. By way of example, several stent devices and methods can be found in commonly assigned and commonly owned U.S. Pat. No. 5,158,548 (Lau et al.); U.S. Pat. No. 5,242,399 (Lau et al.); U.S. Pat. No. 5,344,426 (Lau et al.); U.S. Pat. No. 5,421,955 (Lau et al.); U.S. Pat. No. 5,514,154 (Lau et al.); and U.S. Pat. No. 5,360,401 (Turnlund et al.), which are incorporated in their entirety herein.

More recent devices and procedures for preventing restenosis after arterial intervention employ the use of a radiation source to minimize or eliminate proliferation of cells which is thought to be a major factor in the restenotic process. Balloon catheters have been suggested as a means to deliver and maintain the radiation source in the area where arterial intervention has taken place, exposing the area to a sufficient radiation dose to abate cell proliferation. Two devices and methods are described in International Publication No. WO 93/04735 (Hess) and WO 95/19807 (Weinberger). Other devices and methods which utilize radiation treatment delivered by an intravascular catheter are disclosed in commonly-owned and assigned co-pending U.S. Ser. No. 08/654,698, filed May 29, 1996, now abandoned entitled Radiation-Emitting Flow-Through Temporary Stent, which is incorporated herein by reference. Another medical device for the treatment of a body lumen by radiation is disclosed in European Patent App. 0 688 580 A1 (Schneider).

In the Schneider device, the balloon catheter includes a lumen that extends from a proximal opening to an area near the distal end of the catheter, where it "dead ends." This lumen, known as a "blind" or "dead end" lumen, is intended to carry a radioactive tipped source wire that slides into the lumen once the catheter is in place in the artery or body lumen. When the source wire is positioned, the radioactive section at the distal tip lies near the dead end to provide radiation to the body lumen.

The balloon catheter in the Schneider reference utilizes rapid exchange technology in which the catheter has a distal end guide wire port and a side guide wire port distal to the balloon portion of the catheter. This allows for rapid advancement and replacement of the catheter along the guide wire. Since the length of catheter which glides along the guide wire is relatively short, problems in shaft rigidity and tracking through tortuous, distal arteries can be encountered.

What has been needed and heretofore unavailable in catheters which provide treatment of the body lumen with a radiation source is an intravascular catheter which utilizes rapid exchange technology and has small transverse dimensions, yet provides adequate pushability and trackability for advancement deep into the patient's coronary arteries and across tight stenoses. Such an intravascular catheter would have to be relatively easy and inexpensive to manufacture. Additionally, the radiation source which is to be utilized should be protected from any contact with the patient's bodily fluids, so as to afford multiple use. An additional potential need is to provide blood perfusion distal of the lesion during the radiation process. The present invention fulfills these and other needs.

SUMMARY OF THE INVENTION

This invention is directed to providing improved pushability and trackability over a guide wire of a rapid exchange type intraluminal catheter system which can provide a delivery path for a radioactive source which is centered within the lesion for a period of time sufficient to permit delivery of a radiation source to the body lumen. The increase in trackability and pushability is achieved by utilizing an appropriately tapered reinforcing mandrel disposed within the catheter body which provides the benefits of increased pushability and strength associated with fixed wire catheters with the advantages of tracking over a guide wire as provided by over-the-wire-type catheters.

The catheter system of the present invention generally comprises an elongated catheter body having proximal and distal ends, a guide wire lumen extending through a portion of the catheter body, a first guide wire port in the distal end of the catheter body and a second guide wire port spaced a short distance from the distal end of the catheter body, with both of these guide wire ports being in communication with the guide wire lumen.

A blind lumen disposed in the elongated catheter body from or near the proximal end of the catheter body and terminating at a position near the distal end is adapted to receive a radiation source wire which provides the radiation dosage to the desired area in the patient's body lumen. This blind lumen (or "dead end" lumen) is sealed to prevent entry of the patient's bodily fluids, such as blood, into the blind lumen, and serves as a sterile barrier between a non-sterile source wire and the patient. This blind lumen allows advancement of a radiation source wire from the proximal end of the catheter body to a location near the distal end of the blind lumen and within the inflatable member of the catheter. When the inflatable member is expanded into contact within the body lumen, the radiation source wire will be centered in the body lumen to provide a radiation dose which can be more evenly distributed. The catheter may also permit perfusion of blood flow past the inflatable member during the administration of the radiation dosage, thereby allowing longer periods of radiation exposure. As a result, lower levels of radiation can be used for longer periods of time to provide the necessary dosage.

An inflatable member, such as a balloon, may be provided on the distal section of the catheter body which has an interior in fluid communication with an inflation lumen which extends from the proximal end of the catheter body.

A reinforcing mandrel is disposed within the elongated catheter body for increasing the pushability and stiffness of the catheter body as it is tracked along a guide wire. The portion of the mandrel which extends into the distal portion of the catheter body (e.g., about the distal 10–50 cm) has a smaller transverse dimension than the proximal portion of the mandrel. This provides flexibility in the distal portion of the catheter body, which enters into the coronary artery, and allows the catheter to track over the guide wire while maintaining excellent pushability. In this manner, the catheter has the advantage of tracking over a guide wire as a conventional over the wire system while having the strength and pushability of a fixed wire catheter.

The inflation balloon is configured to be flexible so that it can be expanded on a curved portion of a body lumen, such as a coronary artery. It is also configured to center the radiation source wire within the body lumen, even if the expandable region is positioned on a curved section of the body lumen.

The intravascular catheter of the present invention allows for an over-the-wire delivery for the advancement thereof of the elongated catheter body to a location within a body lumen where the radiation dose is to be administered. The reinforcing mandrel provides additional pushability which is particularly suitable for dilating distal stenoses within small diameter coronary arteries and across tight lesions.

In one particular embodiment of the present invention, the reinforcing mandrel can be disposed within the blind lumen of the catheter body where it can be removed once the catheter has been placed in the particular body lumen where the radiation therapy is to be provided. After the catheter is in place, the reinforcing mandrel can be removed from the blind lumen, allowing the radiation source wire to be inserted into the blind lumen and positioned in the area where the radiation is to be provided. Alternatively, the reinforcing mandrel can be permanently fixed within the catheter body by firmly securing the proximal end of the mandrel within an adapter mounted on the proximal end of the catheter shaft.

These and other advantages of the present invention will become more apparent from the following detailed description thereof when taken in conjunction with the accompanying exemplary drawings.

BRIEF DESCRIPTION OF THE DRAWINGS

FIG. 1B is a cross-sectional view of the inflatable member of the catheter of FIG. 1, in which the inflatable member is expanded within the curved section of artery, thereby centering the radiation source wire within the artery.

FIG. 2 is a cross-sectional view of the catheter of FIG. 1 taken along lines 2—2.

FIG. 3 is a cross-sectional view of the catheter of FIG. 1 taken along lines 3—3.

FIG. 4 is an cross-sectional view of an embodiment of an intravascular catheter of rapid exchange design embodying features of the present invention.

FIG. 5 is a cross-sectional view of the inflatable member of an embodiment of rapid exchange design embodying features of the present invention.

FIG. 6 is a cross-sectional view of the intravascular catheter of FIG. 5 taken along lines 6—6.

DETAILED DESCRIPTION OF THE PREFERRED EMBODIMENTS

The present invention provides a rapid exchange type intravascular catheter for delivering and maintaining a low dose radiation source to the patient's body lumen, such as a coronary artery, for a specified period of time. The catheter assembly includes a reinforcing mandrel which provides excellent pushability and strength to the catheter as it tracks over a guide wire, while still providing sufficient flexibility for trackability in the distal region of the catheter. While the invention is described in detail as applied to the coronary arteries, those skilled in the art will appreciate that it can also be used in other body lumens as well, such as peripheral arteries and veins. Where different embodiments have like elements, like reference numbers has been used.

Figure 1:
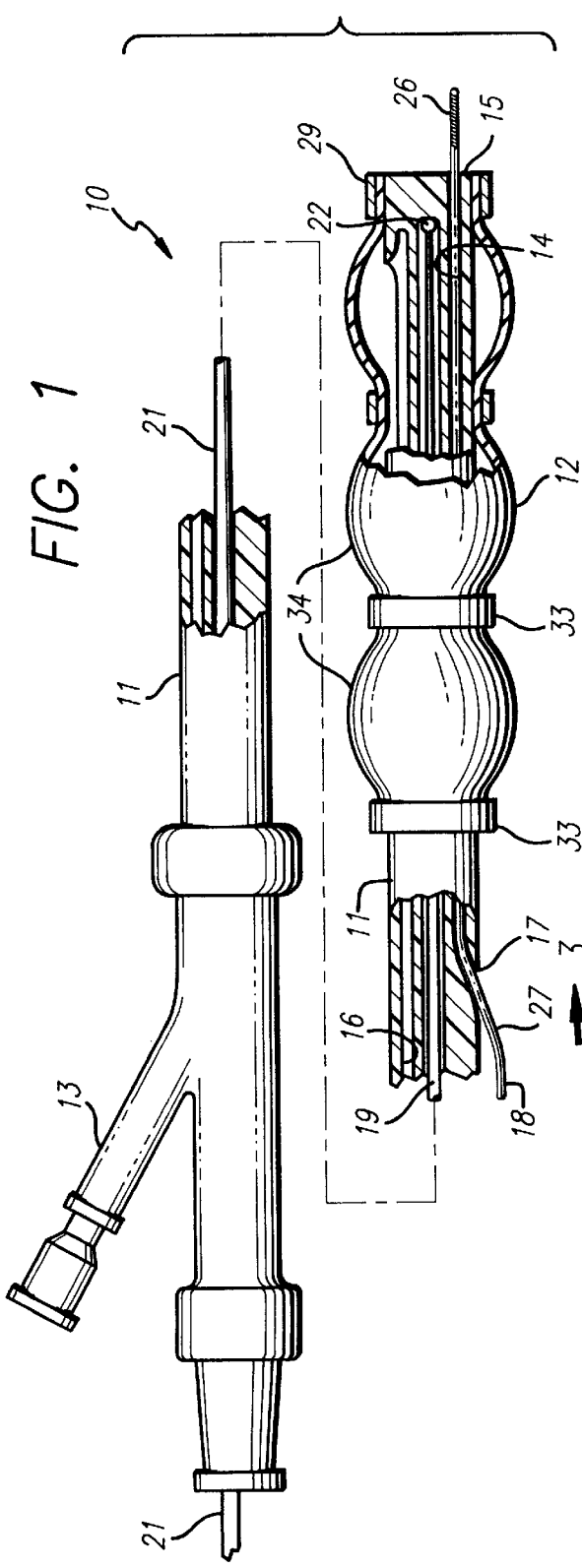
FIG. 1 is an elevational view, partially in cross-section, of an intravascular catheter of rapid exchange design embodying features of the present invention.
Figure 1A:
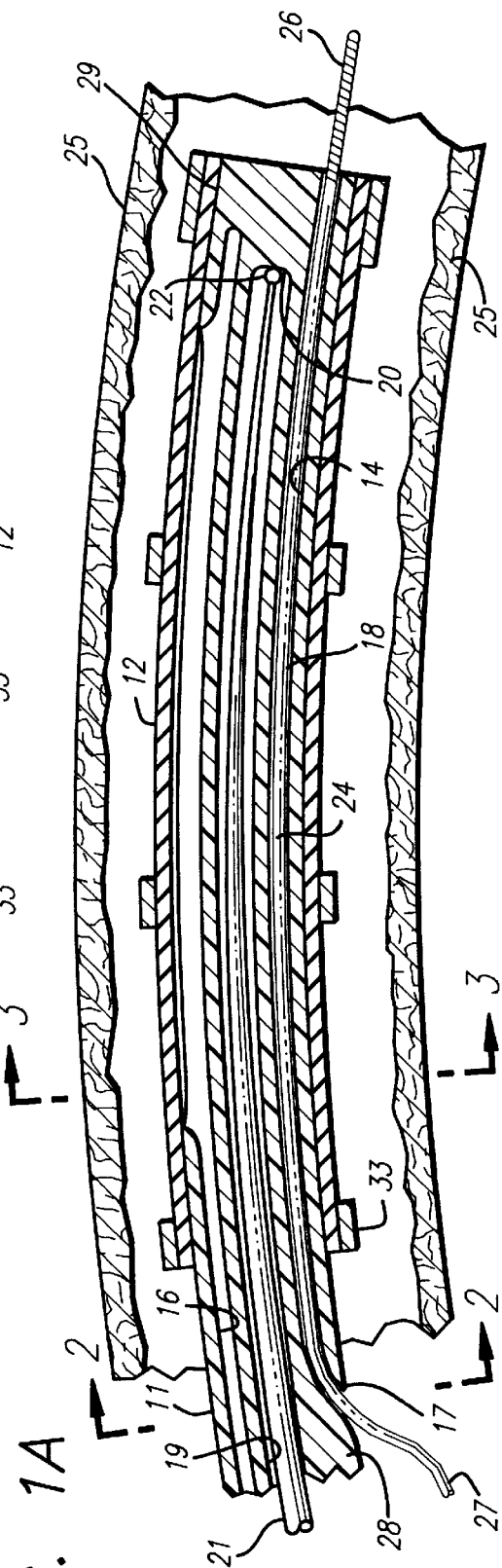
FIG. 1A is a cross-sectional view of the inflatable member of the catheter of FIG. 1, showing the inflatable member in its unexpanded position as it would be placed within a curved section of artery where a radiation treatment is to be provided.

FIGS. 1–3 illustrate an intravascular catheter assembly 10 embodying features of the invention. The catheter assembly 10 generally includes an elongated catheter body 11 with an inflatable member, such as an inflatable balloon 12, on the distal portion thereof and an adapter 13 on the proximal end thereof. An inflation lumen 16 terminates at the proximal end of the balloon 12 and is in fluid communication with the interior of the balloon.

The elongated catheter body 11 includes a guide wire lumen 14 positioned in the distal portion of the elongated catheter body 11 which extends from a first side guide wire port 15 at the distal end of the elongated catheter body 11 and a second guide wire port 17 located in the side wall of elongated catheter body 11. Both of these guide wire ports 15 and 17 are in fluid communication with the guide wire lumen 14. A guide wire 18 is slidably disposed within the relatively short guide wire lumen 14 to facilitate the rapid advancement and replacement of the catheter assembly 10. Further details of rapid exchange catheters can be found in U.S. Pat. Nos. 5,458,613; 5,180,368; 5,496,346; 5,061,273; and 4,748,982, which are incorporated herein by reference.

A blind lumen 19, which is provided within the catheter body 11, extends from the proximal end of the catheter body to a location near the distal end of the inflatable balloon 12. This blind lumen 19 is closed off at its distal end 20 to seal it from entry by any body fluids such as blood, and to provide a sterile barrier between a source wire (which can be reusable and non-sterile) and the patient's vascular system. In keeping with the invention, as can be seen in FIG. 1, a reinforcing mandrel 21 is disposed within the blind lumen for improving the pushability and strength of the catheter assembly as it tracks over the guide wire 18. A small ball 22 may be formed at the tip of the reinforcing mandrel 21 to prevent the mandrel 21 from piercing the distal end 20 of the blind lumen 19.

After the catheter is positioned, the mandrel 21 can be removed from the blind lumen 19 and a radiation source wire 23 can to be inserted into the blind lumen 19 for a period of time sufficient to provide the radiation dose to the body lumen, as is depicted in FIG. 1B. Preferably, the radiation source wire 23 is hollow at its distal end and contains a radiation dose in the form of a radiation source 24, such as pellets, radiation gas, or radioactive liquid or paste. Radiation source wire 23 also may have a radioactive source coated on its distal end. The radiation source wire provides the necessary dosage of radiation to the areas of the artery 25 where arterial intervention has been performed (either by PTCA, atherectomy, stenting or other means) to help abate the growth of cells in this region.

Guide wire 18, which is slidably disposed within the guide wire lumen 14, has a coil 26 on its distal end which is shown in FIG. 1 extending out of the first guide wire port 15 and an elongated core member 27 which is shown extending out of the second guide wire port 17, as would be utilized in a rapid exchange mode. An incline or ramp 28 is provided at the proximal end of the guide wire lumen 14 at the entry way of the second guide wire port 17 to facilitate the insertion and withdrawal of the guide wire 18 therethrough.

In the embodiment shown in FIGS. 1–3, the distance between the distal end 29 of the inflatable balloon 12 and guide wire port 15 should be about 3 to 10 cm, but not greater than 60 cm, and preferably from about 20 to about 50 cm, so that when the balloon is expanded within the patient's vascular system guide wire port 17 of the elongated catheter body 11 will remain within the interior of a guiding catheter to ensure that guide wire 18 does not have the opportunity to form a loop when the catheter assembly 10 is pulled back into the guiding catheter.

Generally, the dimensions of the catheter assembly of the present invention are essentially the same dimensions of vascular catheters used in angioplasty procedures. The overall length of the catheter may be about 100 to 175 cm when a Seldinger approach through the femoral artery is employed. The diameter of the catheter body may range from about 0.030 to 0.065 inches. The balloon 12 in the unexpanded condition has approximately the same diameter as a catheter body, but may be expanded to a maximum diameter of about 1 to about 5 mm for coronary arteries and substantially larger, e.g., 10 mm, for peripheral arteries. The diameter of the guide wire lumen 14 should be sufficiently larger than the diameter of guide wire 18 to allow the catheter to be easily advanced and removed over the guide wire. Additionally, the diameter of the blind lumen 19 should be sufficiently larger than the diameter of the reinforcing mandrel 21 or radiation source wire 23 to allow these two devices to be easily advanced and removed from within the blind lumen 19.

In the preferred method of delivering a radioactive dose to a coronary artery, guide wire 18 is positioned across the portion of the arterial passageway where a PTCA or atherectomy procedure has been performed. The proximal end of the guide wire is advanced through the interior of the guide wire lumen 14 through guide wire port 15 and then outside of guide wire port 17. The catheter is then advanced over the guide wire through a previously positioned guiding catheter to a desired location within the patient's blood vessel, usually where a prior vascular intervention procedure has been performed. A tapered reinforcing mandrel 21 is disposed within the catheter body, usually in the blind lumen 19, in order to provide additional pushability and strength, along with appropriate distal flexibility for track, as the catheter is advanced over the guide wire to the desired location in the artery 25. Initially, the inflatable balloon 12 is in its unexpanded position to allow the catheter to reach the particular area in the artery 25. Depending upon the particular design utilized, the ball 22 on the end of the reinforcing mandrel 21 may come in contact with the distal end 20 of the blind lumen 19 to provide an additional pushing force as the catheter tracks along the guide wire into the tortuous and narrow passageways of the artery.

Once the catheter reaches the desired location, the inflatable balloon 12 is expanded, as shown in FIG. 1B, with the walls of the balloon 31 of the inflatable balloon 12 coming in contact with the wall 32 of the artery 25. The reinforcing mandrel 21 can be removed from the blind lumen 19 before or after inflating the balloon. The radiation source wire 23 can then be inserted into the proximal end of the blind lumen 19 and advanced until the radiation source 24, located near the distal end of the radiation source wire 23, is positioned in the target region to receive the radiation dose. The inflatable balloon 12 is held in an expanded condition for a time sufficient to allow the radiation dose to affect those cells which would otherwise cause restenosis to develop. Preferably, a sufficient dose of radiation can be delivered from about one minute to about sixty minutes to prevent development of restenosis. In its expanded condition, the inflatable balloon presses against, or at least comes in close proximity to, the walls of the artery and in doing so centers the radiation source wire within the artery. Centering of the radiation dose is important so that all portions of the artery receive as close to uniform and equal amounts of radiation as possible. Also, centering helps prevent radiation burns or hot spots from developing on portions of the target area.

After the radiation dose has been administered to the body lumen, the radiation source wire 23 can be removed, the inflatable balloon 12 deflated, and the entire catheter assembly 10 withdrawn from the patient's vasculature.

Multiple support collars 33 located on the outside of the inflatable balloon 12 divide the balloon into individual sections 34 which help center the catheter shaft with the balloon, assuring that an equal amount of a radiation dosage is provided to the body lumen. These individual sections 34 also assist in the centering of the balloon and radiation source wire 23 when the target area is at a curved portion of the patient's vascular, again helping to maintain an equal dosage to the body lumen. Alternatively, a series of short balloons may be formed individually and heat-sealed (or adhesively attached) to the catheter shaft without the need for collars 33. Still another option is to form a series of short balloons on a single tubing, which is then appropriately sealed to the catheter shaft.

Preferably, the portion of the mandrel 21 which extends into the distal portion of the catheter has smaller transverse dimensions than the proximal portion of the mandrel. The smaller diameter portion of the mandrel which extends into the distal portion of the catheter body preferably has transverse dimensions at least 20 percent less than the transverse dimensions of the proximal portion of the mandrel. This provides flexibility in the distal portion of the catheter and allows the catheter to track over the guide wire while maintaining excellent pushability.

In some instances, the reinforcing mandrel may be permanently fixed or enclosed within the catheter body, or it may be removable. The mandrel can be fixed within the catheter body by suitable means such as firmly securing the proximal end of the mandrel within the adapter 13 mounted on the proximal end of the catheter body. Also, the mandrel may have several sections which have sequentially smaller diameters (sequentially smaller diameters in the distal direction) which can be provided with tapers between the various-sized sections. This allows varying degrees of strength and flexibility up to the catheter shaft as is necessary. Preferably, the distal 10 to 40 cm of the mandrel will have reduced dimensions obtained, for example, by a continuous or stepwise grinding profile. Generally, more gradual changes in dimension are preferred to provide optimal transmission of push to the tip of the catheter and optimum trackability. Further details of the construction of reinforcing mandrels can be found in U.S. Pat. No. 5,242, 396, which is incorporated herein by reference.

In another preferred embodiment of the invention, as shown in FIG. 4, the catheter assembly includes a guide wire lumen 14' in which the second guide wire port 15 is located distal to the inflatable balloon 12. In this particular embodiment, the length of the lumen 14' is even shorter than the lumen shown in FIG. 1 (e.g., about 0.5 cm to about 3 to 10 cm), and the catheter benefits even more from the presence of the reinforcing mandrel 21 to help increase the pushability and strength of the catheter as it tracks over the guide wire 18.

In another embodiment of the invention, as is shown in FIGS. 5 and 6, the catheter assembly 10 includes a guide wire lumen 14 in which a perfusion port 35 is provided in the catheter shaft proximal to the inflatable balloon 12 and perfusion port 36 is provided in the catheter body distal to the inflatable balloon. These particular perfusion ports 35 and 36 help to permit the flow of blood through the guide wire lumen 14 when the balloon is inflated to permit blood perfusion during the radiation therapy. Additional perfusion ports and perfusion lumens could be added to allow increased blood flow past the inflatable balloon, allowing the catheter to be maintained in the artery for a longer period of time thereby eliminating or preventing ischemia during the treatment. Alternatively, spiral or ribbed balloons, or other similar centering means, could be employed to allow perfusion over or through the centering means. For example, an expandable metal cage could be used as a centering device. Such a cage would allow blood flow through the lattice of the cage.

The catheter assemblies of the invention as described herein are generally employed after an atherectomy, percutaneous transluminal coronary angioplasty procedure, or stent implantation to allow a radiation dose to be administered to an area where restenosis might otherwise develop in the coronary artery. It should be recognized by those skilled in the art that the catheter of the present invention can be used within a patient's vasculature system after vascular procedures other than a PTCA, a stent implantation or an atherectomy have been performed.

The catheter assembly of the present invention may be formed of conventional materials of construction which are described in detail in the prior art patents referenced herein. The materials formed in the catheter body and the inflatable balloon can be made out of relatively inelastic materials, such as polyethylene, polyvinyl chloride, polyesters and composite materials. The various components may be joined by suitable adhesives such as the acrylonitrile based adhesive sold as Loctite 405. Heat shrinking or heat bonding may also be employed where appropriate. Additionally, the present invention can be made with a balloon material that is distensible since compression of plaque for this particular application is not required. The reinforcing mandrel can be made from a stainless steel, NiTi alloys, or other suitable materials such as high strength plastic. The tapers and small diameter portions of the mandrel can be formed in the same manner as that used in forming small diameter sections on guide wires, e.g., centerless grinding. Plastic to plastic or plastic to metal joints can be effected by a suitable adhesive such as Loctite 405. Additionally, the radiation source wire can be made from similar materials such as stainless steel, titanium, nickel titanium and platinum nickel alloys or any suitable polymers and composites. Variations can be made in the composition of the materials to vary properties.

As described herein, the catheter assembly will deliver a low dosage of radiation through the body lumen, such as a coronary artery, and is configured to provide the dosage over longer periods of time if necessary. It is preferred that a low dosage of radiation, on the order of 0.1 up to 3.0 curies be the typical radiation dose provided to treat, for example, a coronary artery. Preferably, 1 to 2 curies will provide a proper dosage level.

The radiation delivered to a coronary artery should be in the range from about 20 to 3,000 rads and preferably not less than thirty seconds. The radiation dose can be delivered in less than thirty seconds, however, it is preferable that a longer time frame be used so that a lower dose can be administered.

It is contemplated that different radiation sources can be used, and the preferred radiation sources include iridium$^{192}$ if alpha radiation is used, and phosphorus$^{32}$ if beta particles are used. Further, it is contemplated that the radiation sources may provide beta particles or gamma rays to affect the target cells. However, alpha emitting radiation sources also can be used even though such radiation does not travel very far in human tissue. The use of beta and gamma emitting radiation sources is well known for treating and killing cancerous cells. Other modifications can be made to the present invention without departing from the spirit and scope thereof. The specific dimensions, doses, times and materials of constructions are provided as examples and substitutes are readily contemplated which do not depart from the invention.

What is claimed is:

1. An intravascular catheter for delivering and maintaining a radioactive dose in a body lumen, comprising:
    an elongated catheter body having a proximal end and a distal end;
    an inflation lumen extending within the elongated catheter body to a location on a distal portion of the elongated body;
    an inflatable member disposed on the distal portion of the elongated catheter body and having an interior in fluid communication with the inflation lumen;
    a guide wire lumen extending through a portion of the elongated catheter body for receiving a guide wire;
    a first guide wire port in the distal end of the catheter body in communication with the guide wire lumen and a second guide wire port in the distal portion of the catheter body which is spaced a short distance from the distal end of the catheter body and a substantial distance from the proximal end of the catheter body and which is in communication with the guide wire lumen;
    a blind lumen extending within the elongated catheter body from the proximal end of the catheter body and terminating at a position near the distal end of the inflatable member, the blind lumen adapted to receive a radiation source wire; and
    a reinforcing mandrel disposed within the elongated catheter body for increasing the pushability and stiffness of the catheter body as it is tracked along a guide wire.

2. A catheter assembly for delivering and maintaining a radioactive dose in a body lumen comprising:
    an elongated catheter body having a proximal end and a distal end;
    an inflation lumen extending within the elongated catheter body to a location on a distal portion of the elongated body;
    an inflatable member disposed on the distal portion of the elongated catheter body and having an interior in fluid communication with the inflation lumen, the inflatable member having a plurality of spaced apart inflatable sections;
    a guidewire lumen extending through a portion of the elongated catheter body for receiving a guidewire;
    a first guidewire port in the distal end of the catheter body in communication with the guidewire lumen and a second guidewire port in the distal portion of the catheter body which is spaced a short distance from the distal end of the catheter body and a substantial distance from the proximal end of the catheter body and which is in communication with the guidewire lumen;
    a blind lumen extending within the elongated catheter body from the proximal end of the catheter body and terminating at a position near the distal end of the inflatable member, the blind lumen adapted to receive a radiation source wire; and
    a reinforcing mandrel disposed within the elongated catheter body for increasing the pushability and stiffness of the catheter body as it is tracked along a guidewire.

3. The catheter assembly of claim 2, wherein the plurality of spaced apart inflatable sections are configured to provide flexibility at the catheter distal end.

4. The catheter assembly of claim 3, wherein the plurality of spaced apart inflatable sections are formed from a single inflatable member.

5. The catheter assembly of claim 2, wherein the plurality of spaced apart inflatable sections are adjacent to each other.

6. The catheter assembly of claim 2, wherein the elongated catheter body is an over-the-wire configuration.

7. The catheter assembly of claim 2, wherein the elongated catheter body is a rapid exchange configuration.

* * * * *